Jan. 8, 1974 B. E. GRAUST Plant Pat. 3,430
CARNATION PLANT
Filed March 6, 1972
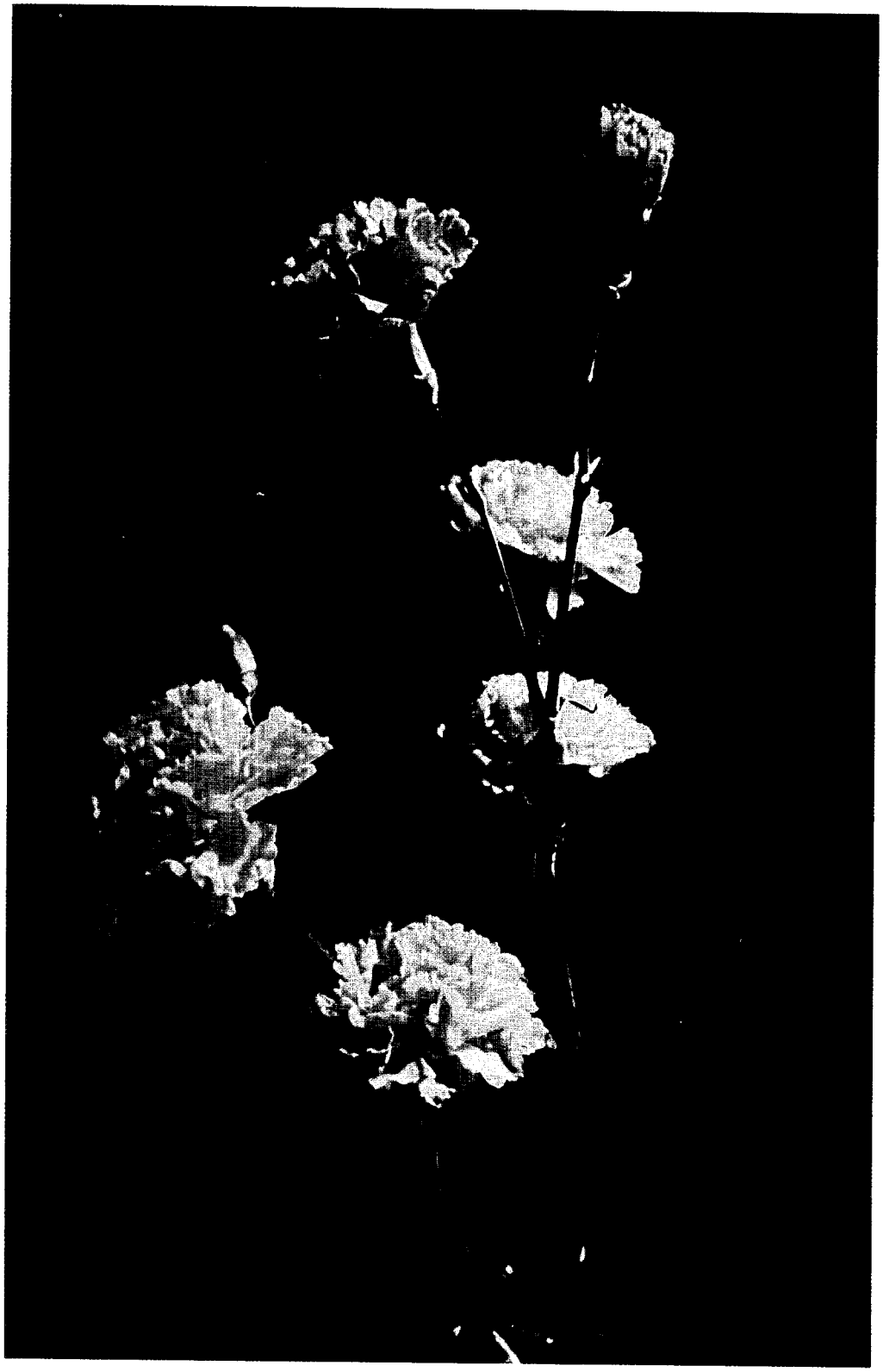

United States Patent Office

Plant Pat. 3,430
Patented Jan. 8, 1974

3,430
CARNATION PLANT

Bent E. Graust, 3233 Freedom Blvd.,
Watsonville, Calif. 95076

Filed Mar. 6, 1972, Ser. No. 232,296
Int. Cl. A01h 5/00
U.S. Cl. Plt.—73 1 Claim The present invention relates to a new and distinct variety of carnation plant characterized particularly by the unique color of its flower.

The new variety was found as a mutation of the well-known variety, "Elegance" registered with the American Carnation Society on Feb. 16, 1959.

The original reproduction by cuttings was carried out at my commercial greenhouse in Watsonville, Calif. Cuttings have been taken from 1969 through 1971 and have been found to consistently produce flowers with the new and distinctive color.

The accompanying drawing shows typical specimens of the new variety in different stages of development and in color as nearly true as is reasonably possible to make.

The following is a detailed description of the new carnation using the Reinhold Color Atlas by A. Kornerup and J. H. Wanscher, published by the Reinhold Publishing Corporation, New York, N.Y. (Library of Congress Catalog Number 62–8756):

The new variety is three to four inches taller than its parent, "Elegance." The petals of the new variety have a uniform color with both upper and lower surfaces the same. The color is bluish red, as shown at Plate 12, Swatch A8, of the aforementioned Reinhold Color Atlas. In all other respects the new variety is the same as its parent "Elegance."

I claim:

1. The new and distinct variety of carnation substantially as herein disclosed characterized as to novelty by the color of its flower.

No references cited.

ROBERT E. BAGWILL, Primary Examiner